United States Patent [19]
Heemann et al.

[11] Patent Number: 5,119,835
[45] Date of Patent: Jun. 9, 1992

[54] METHOD FOR EXTRACTING TOBACCO ALKALOIDS

[75] Inventors: Volker Heemann, Reinbek; Gerald Schmekel; Uwe Ehling, both of Elmshorn; Bernhard Hauser, Schenefeld; Casper H. Koene; Helge Rabitz, both of Hamburg, all of Fed. Rep. of Germany

[73] Assignee: B.A.T. Cigarettenfabriken GmbH, Fed. Rep. of Germany

[21] Appl. No.: 647,072

[22] Filed: Jan. 29, 1991

[30] Foreign Application Priority Data

Jan. 31, 1990 [DE] Fed. Rep. of Germany ....... 4002784

[51] Int. Cl.⁵ ............................................. A24B 15/24
[52] U.S. Cl. .................................. 131/297; 131/298; 131/900
[58] Field of Search ........................ 131/297, 298, 900

[56] References Cited

U.S. PATENT DOCUMENTS

| | | | |
|---|---|---|---|
| 2,293,954 | 8/1942 | Tiger et al. | 131/297 |
| 4,506,682 | 3/1985 | Muller | 131/298 |
| 4,727,889 | 3/1988 | Niven, Jr. et al. | 131/297 |
| 4,898,188 | 2/1990 | Niven, Jr. et al. | 131/298 |
| 5,018,540 | 5/1991 | Grobbs et al. | 131/298 |

FOREIGN PATENT DOCUMENTS

| | | |
|---|---|---|
| 280817 | 9/1988 | European Pat. Off. . |
| 124725 | 1/1901 | Fed. Rep. of Germany . |
| 2142205 | 3/1973 | Fed. Rep. of Germany . |
| 2043537 | 1/1975 | Fed. Rep. of Germany . |
| 2844781 | 10/1978 | Fed. Rep. of Germany . |
| 3334736 | 4/1985 | Fed. Rep. of Germany . |

Primary Examiner—V. Millin
Assistant Examiner—Lynne Reichard
Attorney, Agent, or Firm—Armstrong, Nikaido, Marmelstein, Kubovcik & Murray

[57] ABSTRACT

A method is described for extracting tobacco alkaloids from tobacco in which the tobacco alkaloids are extracted from the tobacco with carbon dioxide under supercritical conditions and the tobacco alkaloids separated from the carbon dioxide, wherein in the carbon dioxide for the extraction of the tobacco alkaloids from the tobacco is mixed with a solid 2 to 3-basic organic acid having a total of 2 to 6 carbon atoms, a monoalkali or monoammonium salts thereof in order to appreciably shorten the extraction times.

17 Claims, 1 Drawing Sheet

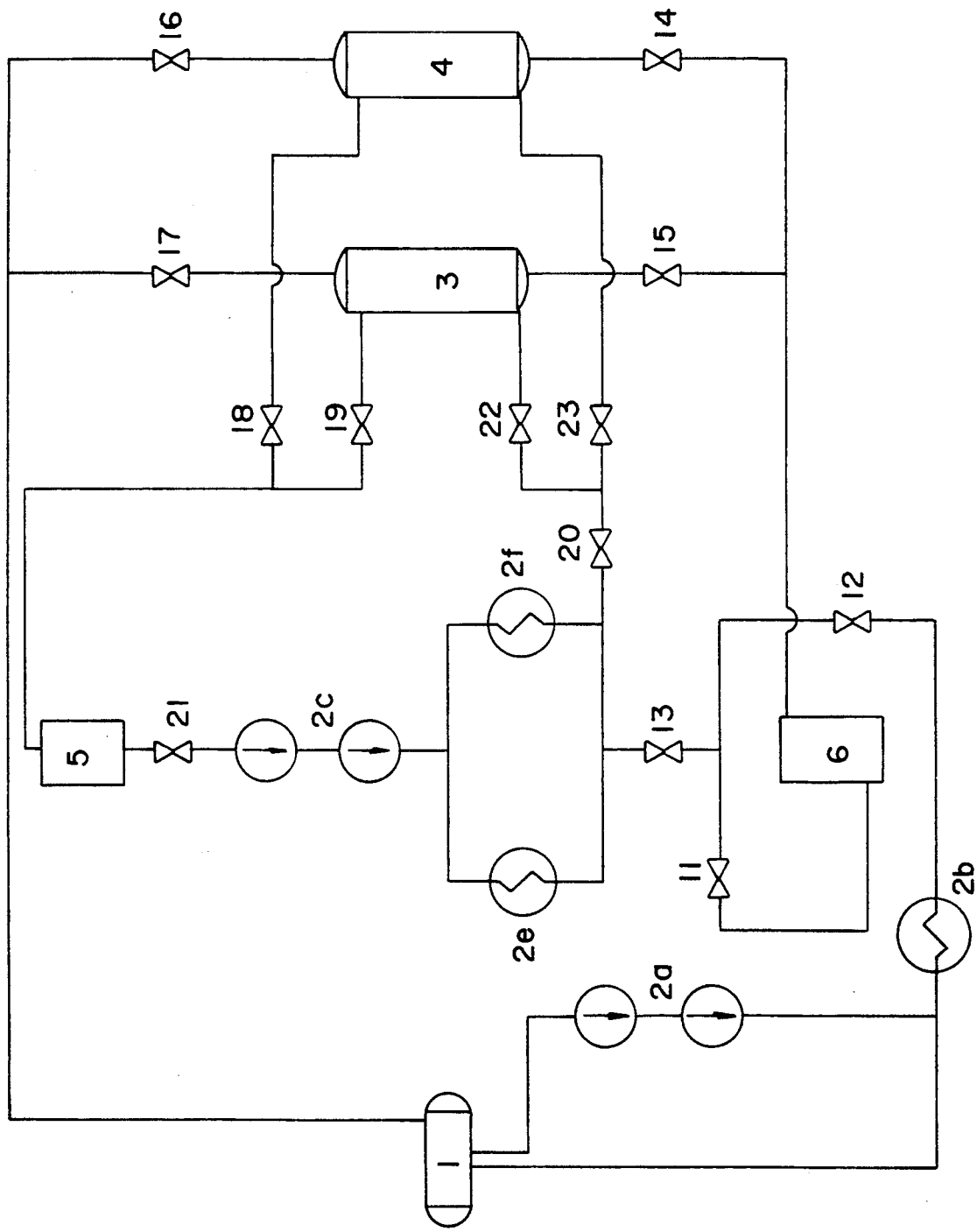

5,119,835

METHOD FOR EXTRACTING TOBACCO ALKALOIDS

BACKGROUND OF THE INVENTION

1. Field of the Invention

The invention relates to a method of extracting tobacco alkaloids from tobacco. In particular, the invention relates to a method with which nicotine is extracted from tobacco.

2. Description of the Prior Art

The extraction of tobacco alkaloids from tobacco has been known for a long time in the art. Extractive methods using organic or aqueous solvents play an important part therein. In particular, the objective of various processes is the extraction of nicotine using such organic or aqueous solvents. The disadvantages of these methods is that the extraction is nonspecific and varying amounts of flavours are extracted from the tobacco along with the nicotine.

In addition, such extraction methods also have a negative effect on the structure of the tobacco and influence in undesirable manner the flavour of the smoke arising when such tobacco burns. Separation of the extracts obtained in the extraction and subsequent recombination of the fraction containing the flavours with the tobacco is very complicated.

Tobacco alkaloids, in particular nicotine, can be extracted selectively using solvents in the supercritical state. For this purpose, carbon dioxide has preferably been used. In German patent specification 2,043,537 a method is described in which nicotine is extracted from tobacco by means of $CO_2$ in the supercritical state. The separation of the nicotine from the extract can be achieved either with sorbents or by expanding the extract mixture. Due to the relatively poor solubility of nicotine, long extraction times are necessary. They have disadvantageous effects on the smoke flavour of the subsequent burning tobacco when smoked.

German patent specification 2,142,205 describes a multistage method for removing nicotine from tobacco. Firstly, the flavours are extracted from dry tobacco with carbon dioxide in the supercritical state. Thereafter, the tobacco is brought into contact with moist carbon dioxide in the supercritical state, nicotine being extracted thereby. In the third method step the tobacco is again mixed with the flavours which were extracted in the first step. As in the method described above, the long process times lead to impairment of flavour and prevent an economic process.

To reduce the coextraction of flavours in the denicotinizing, a mixture of nitrogen and carbon dioxide under supercritical conditions can be used for the extraction (German Offenlegungsschrift 3,334,736). In German Offenlegungsschrift 2,844,781 it is proposed to increase the effectiveness and specificity of the extraction step by a combination of a gaseous (carbon dioxide) and a liquid (ethanol) component. These methods also have the disadvantage that due to the low solubility of nicotine in supercritical carbon dioxide, process times of several hours are required and these are contrary to an economic application of this extraction method. The extraction by the methods indicated above moreover leads to considerable losses of tobacco quality and smoke flavour.

EP-A 0 280 817 describes a method of extracting nicotine from tobacco and tobacco mixtures using supercritical or liquid extraction agents. The tobacco is brought into contact with extraction agents, inter alia also with carbon dioxide, to extract nicotine and also other tobacco ingredients. The nicotine is separated from the extract by passing the latter through a vessel containing a non-volatile acid or a salt of said acid. The flavour components pass through said vessel together with the extraction agent whilst the nicotine is chemically bonded in the vessel to the acid or the salt and thereby separated from the carbon dioxide.

A disadvantage of the method disclosed in EP-A 0 280 817 resides in that the non-volatile acid or salt of said acid necessary for bonding the nicotine must be attached to suitable carrier materials, for example shells of caco beans. In addition, the treatment vessels, in particular the pressure vessels, must be made very large because for separating the nicotine from the extract the acid or its salt (and thus also the necessary carrier materials) must be used in a ratio of at least 1:1, preferably however >1:1.

In EP-A 0 280 817 it is moreover stated that the non-volatile acids suitable for separation of the nicotine from the extract by chemical bonding must not be soluble in the extraction solvent used under the extraction conditions. Consequently, salts of non-volatile acids having a particularly low solubility are especially preferred. This is apparently intended to avoid acid or salt being able to leave the separating vessel and penetrate into the extraction cycle.

SUMMARY OF THE INVENTION

The present invention therefore has as its object the provision of a method with which tobacco alkaloids can be separated from tobacco by extraction in a manner which is simple and harmless to the tobacco raw material. In particular, a method is to be proposed which does not extract flavours from the tobacco but can effect a selective extraction of specific tobacco alkaloids, in particular nicotine. From the point of view of the subsequent use of the tobacco, the invention has as its objective in particular short treatment times which eliminate any risk of impairing the tobacco quality. The invention also aims at using physiologically harmless solvents with a low kilogram price.

Surprisingly, it has been found that certain non-volatile organic acids or their monoalkali metal salts have an hitherto unknown solubility in super-critical carbon dioxide (pressure: about 250 bar, temperature: about 70° C.). A further surprising result of the invention resides in that under the process conditions the solubility of nicotine in supercritical carbon dioxide increases by a factor of 3 to 5 when the carbon dioxide contains certain amounts of such non-volatile organic acids or their monoalkali metal or monoammonium salts. This makes it possible to reduce the extraction times necessary for the extraction of tobacco alkaloids in particular of nicotine, so that the process-technological, economic as well as flavour disadvantages of the known methods are eliminated.

The invention therefore proposes a method of extracting tobacco alkaloids from tobacco in which the tobacco alkaloids are extracted from the tobacco with carbon dioxide under supercritical conditions and the tobacco alkaloids are separated from the carbon dioxide, wherein a solid, 2 to 3-basic organic acid having a total of 2 to 6 carbon atoms, a monoalkali metal or monoammonium salt thereof, or a mixture thereof, is dissolved in the carbon dioxide for the extraction of the tobacco alkaloids from the tobacco.

With the method according to the invention, various tobacco alkaloids can be selectively extracted from tobacco of any origin. Particularly preferred nicotine is extracted from tobacco. Although the method according to the invention is not restricted to the extraction of nicotine, it will be explained in detail below with reference to that preferred example.

According to the invention, in the carbon dioxide for the extraction of the tobacco alkaloids from the tobacco, a solid 2 to 3-basic organic acid having a total of 2 to 6 carbon atoms is dissolved. Examples of such acids are oxalic acid, malonic acid, succinic acid, glutaric acid, adipic acid, malic acid, tartaric acid, music acid and citric acid.

In accordance with a preferred embodiment of the method according to the invention, instead of said organic acids or also together with said acids one or more monoalkali or monoammonium salt(s) of said acids is-/are dissolved in the carbon dioxide for the extraction of the tobacco alkaloids from the tobacco. As monoalkali salts, lithium, sodium, potassium or rubidium salts can be used. Because of the easy availability, primarily the sodium and/or potassium salts are used. However, in the same manner monoammonium salts may also be used.

In a particularly preferred embodiment of the method an organic salt of the group oxalic acid, malonic acid, malic acid, tartaric acid and citric acid or their monoalkali or monoammonium salts, or a mixture thereof is dissolved in the carbon dioxide for the extraction of the tobacco alkaloids from the tobacco.

Particularly good results may be achieved on adding monoalkali metal oxalates, malonates, malates, tartrates or citrates. The solubility of tobacco alkaloids, in particular nicotine, is surprisingly increased particularly significantly if potassium citrate is added to the carbon dioxide intended for the extraction of the tobacco alkaloids from the tobacco.

The amount of organic acid or salt of the corresponding acid added to the carbon dioxide is critical in so far as an acid amount or salt amount must be added which leads to an improvement, adequate for the practical use, in the solubility of the tobacco alkaloids, in particular nicotine, in the carbon dioxide extraction agent. According to the invention, it is particularly preferred to add to the carbon dioxide for the extraction of the tobacco alkaloids from the tobacco the organic acid or its salts in saturation amounts, i.e. in amounts which lead to a saturation of the corresponding compound or compounds in the carbon dioxide under process conditions. On saturation the maximum possible increase of the solubility of for example, nicotine in the supercritical carbon dioxide is achieved so that the best extraction results may be obtained. This is, for example, for potassium monocitrate about 0,02% by weight with respect to the $CO_2$ used.

BRIEF DESCRIPTION OF THE DRAWING

The invention will be explained hereinafter in more detail with reference to the accompanying single FIG. which shows a flow chart of the method according to the invention.

DESCRIPTION OF THE PREFERRED EMBODIMENTS

This method is carried out in a manner known per se in a plant permitting operation under conditions in which the carbon dioxide extraction solvent is present in the supercritical state. Pressure-resistant containers and plant components of suitable design are known to the expert from the prior art.

In a preferred conduction of the method according to the invention, the liquid carbon dioxide is introduced from a working tank 1 via one or more liquid pumps 2a into the plant. The carbon dioxide is conducted through a heat exchanger 2b to bring it to the process temperature. The latter is usually about 70° C. However, somewhat higher or lowertemperatures are also conceivable.

Prior to the contact with the tobacco, the carbon dioxide is mixed with a solid 2 to 3-basic organic acid having a total of 2 to 6 carbon atoms or with one or more monoalkali or monoammonium salt(s) of such an organic acid or a mixture thereof. In the manner illustrated in the Figure this is done, proceeding from the basic state (all the valves closed), by opening the valves 12 and 11 to allow the supercritical carbon dioxide to flow into an acid or salt container 6. The acid or salt container 6 may be subjected to the carbon dioxide flow in the axial direction or also in radial direction. The container 6 is provided at the inlet and outlet sides with a sieve or screen plate suitable for this purpose which prevents the solid acid or the solid salt flowing out but permits a free passage of the supercritical carbon dioxide, possibly of the supercritical carbon dioxide charged with acid or salt. Possibly, the carbon dioxide may flow through the container several times.

After opening the valves 14, 15, the carbon dioxide mixed with the acid and/or a salt of said acid is pumped by means of the liquid pumps 2a out of the container 6 to the tobacco containers 3 and 4.

The carbon dioxide charged with the acid or one or more of its salts is subsequently brought into intimate contact with the tobacco for extraction of the tobacco alkaloid, preferably nicotine. This is done by conducting it through one or possibly also several, then parallelly-connected, tobacco extraction containers 3, 4. These containers contain the preconditioned tobacco or raw tobacco known in the prior art. If only one container is to be traversed, for example the container 3, the valves 14, 16, 17 and 18 must be closed and the valves 15 and 19 opened. With simultaneous flowing into both containers all the valves 14, 15, 18 and 19 are opened.

The flow approach of the tobacco extraction containers 3 and 4 may be in any desired manner known from the prior art. For example, an axial or a radial flow approach is conceivable. The decisive point is that the tobacco comes into intimate contact with the mixture of supercritical carbon dioxide and added acid dissolved therein or added monoalkali or monoammonium salt dissolved therein. The contact time, i.e. the time during which an extraction of the tobacco alkaloid or alkaloids from the tobacco takes place, is substantially shorter than with conventional methods. According to the invention it is in the range from about 30 to 60 minutes. The contact time is, however, variable on varying the other process parameters and may be slightly more than 60 minutes. However, considerably shorter contact times are also conceivable.

The extract mixture of carbon dioxide, acid or salt dissolved therein and tobacco alkaloid, in particular nicotine, is then supplied to an apparatus 5 for separating the tobacco alkaloids from the mixture. Advantageously, as apparatus for separating the tobacco alkaloids from the extract mixture vessels are chosen in which the tobacco alkaloids can be separated by means of an adsorbent. Possible preferred adsorbents are active charcoal or aluminium silicates suitable for the adsorption. Of said silicates, in particular zeolites have proved suitable. Adsorbers filled with zeolites permit an almost complete separation of tobacco alkaloids, in particular nicotine, in the exchange container 5. The $CO_2$ charged with the organic acid or its salt is not adsorbed at such zeolite exchanger materials but is returned to the cycle again unchanged.

It is, however, also possible to fill the exchange container 5 with a chemisorbent and to separate the tobacco alkaloids by means of a chemisorbent from the extract mixture. Proven and thus preferred chemisorbents are ion exchangers, in particular acidic ion exchangers. The passage of the extract mixture through an exchange container 5 filled with a acidic ion exchanger likewise leads to an almost complete separation of the tobacco alkaloids, in particular the nicotine, from the extract mixture. Thus, only the supercritical carbon dioxide and the acid or its salt dissolved therein leave the container 5.

According to a preferred embodiment of the method, the carbon dioxide acid or salt mixture, on closure of the valves 13, 14, 15 and opening of the valves 20, 22, 23 (after switching off the pumps 2a and closing the valve 12), is conducted by means of the pumps 2c directly to the tobacco container or containers. If necessary, by connecting the container 6 (valves 20, 22, 23 closed, valves 13, 11, 14 and/or 15 opened) an postsaturation can, of course, be effected.

The postsaturation is normally not necessary because salt is not adsorbed either by the tobbaco or by the adsorbent or chemisorbent aqnd the good solubility of the carbon dioxide/acid or salt mixture for the tobacco alkaloid, in particular nicotine, does not appreciably change.

As a result the carbon dioxide/acid or salt mixture is cycled and the extraction cycle starts afresh.

To bring the plant into the starting condition it is necessary to establish pressure balance between the working tank 1 and the container or containers 3, 4 by cooling and via a valve not shown. The valves 16, 17 serve to displace $CO_2$ liquid by $CO_2$ gas: with the aid of the pumps $2_c$ via a conduit, not shown, the liquid $CO_2$ is pumped from the containers 3, 4 back into the working tank 1. The $CO_2$ gas then remaining in the containers is then vented via a release valve, not illustrated.

The path of the method according to the invention preferred and illustrated in the Figure with two tobacco extraction containers permits a quasi-continuous operation. The number of the tobacco extraction containers is, of course, not limited to two. As already indicated above, however, discontinuous operation is also possible; in this case, a single tobacco extraction container 3 is sufficient.

The advantage of the method according to the invention over the methods known in the prior art is to be seen in that due to the improvement of the solubility of the tobacco alkaloids, in particular the nicotine, in the extraction solvent, carbon dioxide, the extraction time can be drastically reduced. The acid or its salt increases the solubility of nicotine in supercritical carbon dioxide by a factor of 3 to 5 (depending on the process conditions). The extraction times are thus reduced to about 30 minutes, thereby avoiding at the same time any impairment of the quality of the tobacco treated.

In contrast to the prior art the acid or its salt are not employed as adsorption agents for separating the nicotine from the extract mixture. On the contrary, they increase the solubility of the tobacco alkaloids, in particular nicotine, in the carbon dioxide. The acid or salt is thus not used up or removed from the method. On the contrary, the tobacco alkaloid or nicotine contained in the extract mixture is deposited in the exchange container without any appreciable deposition of the acid or its salt in the exchange container occurring. The organic acid or, the salt are thus conducted together with the carbon dioxide in the cycle.

The invention will be explained hereinafter with reference to some example.

EXAMPLE 1

25 kg cut tobacco having a moisture content of 25% and an initial nicotine content of 1.98% were taken. Supercritical $CO_2$, mixed with 1.5 kg potassium monocitrate in the supply container and kept so that saturation of the salt in the carbon dioxide was always observed, was conducted through a plant according to the Figure with a volume flow of 5.2 m$^3$/h. The extraction temperature was 70° C. The pressure was 250 bar. The mass flow $CO_2$, with respect to the dry tobacco mass, was $208^{-h1}$. After adjusting the extraction conditions, the nicotine content in the $CO_2$ was 70 mg/kg. The extract mixture was supplied to the exchange container which was filled with 9 kg of an acidic ion exchanger as chemisorbent. The nicotine was completely extracted from the carbon dioxide. After an extraction time of 30 minutes the final nicotine content of the tobacco was about 0.20%.

The residual amount of potassium monocitrate in the supply container at the end of the test was still 1.1 kg.

Thus, during an extraction time of only 30 minutes it was possible to extract from the tobacco used almost 90% of the nicotine and completely remove the latter from the extract mixture.

EXAMPLE 2

The same procedure as in Example 1 was adopted. However, 100 kg tobacco having a nicotine content of 2.50% was employed.

The extract mixture was denicotinized completely thereafter at 10 kg ion exchanger.

COMPARATIVE EXAMPLE

The same procedure as Example 1 was adopted. However, no acid or no salt of such an acid was added to the extraction agent. After adjusting the extraction conditions, the nicotine content in $CO_2$ was 17 mg/kg. The extraction time until reaching a final nicotine content of 0.18% was 14 hours.

Thus, with the method according to the prior art the same result (final nicotine content in the tobacco: about 0.2%) was reached under the same method conditions in a time which is 28 times longer than the extraction time with the procedure according to the invention.

We claim:

1. A method for extracting tobacco alkaloids from tobacco comprising
   (a) mixing carbon dioxide with a solid 2- to 3- basic organic acid having a total of 2 to 6 carbon atoms, a monoalkali metal salt or monoammonium salt of said organic acid, or a mixture thereof, to form an extraction solvent;

(b) contacting tobacco with said extraction solvent under supercritical conditions to thereby extract tobacco alkaloids from the tobacco; and (c) separating the tobacco alkaloids from said extraction solvent.

2. The method of claim 1, wherein said tobacco alkaloid to be extracted from said tobacco is nicotine.

3. The method of claim 1, wherein the tobacco alkaloids are separated from the extraction solvent by means of an adsorbent.

4. The method of claim 3, wherein said adsorbent is selected from the group consisting of active charcoal, aluminum silicate and zeolites.

5. The method of claim 4, wherein said adsorbent is a zeolite.

6. The method of claim 1, wherein the tobacco alkaloids are separated from the extraction solvent by means of a chemisorbent.

7. The method of claim 6, wherein the chemisorbent is an ion exchanger.

8. The method of claim 7, wherein said ion exchanger is an acidic ion exchanger.

9. The method of claim 1, wherein an organic acid selected from the group consisting of oxalic acid, malonic acid, succinic acid, glutaric acid, adipic acid, malic acid, tartaric acid, mucic acid and citric acid, a monoalkali metal salt or monoammonium salt of said organic acid, or a mixture thereof, is mixed with the carbon dioxide to form the extraction solvent.

10. The method of claim 9, wherein a monoalkali metal salt selected from the group consisting of monoalkali metal oxalates, monoalkali metal malonates, monoalkali metal malates, monoalkali metal tartrates, and monoalkali metal citrates is mixed with the carbon dioxide to form the extraction solvent.

11. The method of claim 10, wherein said monoalkali metal. salt is a monoalkali metal citrate.

12. The method of claim 11, wherein said monoalkali metal citrate is potassium monocitrate.

13. The method of claim 1, wherein the organic acid, its monoalkali metal salt or monoammonium salt, or mixture thereof, is added in saturation amounts to the carbon dioxide to form the extraction solvent.

14. The method of claim 1, wherein a monoalkali metal salt is added in saturation amounts to the carbon dioxide.

15. The method of claim 14, wherein the monoalkali metal salt is potassium monicitrate and the concentration of the potassium monocitrate in the carbon dioxide is about 0.02% by weight.

16. The method of claim 1, wherein following separation of the tobacco alkaloids from the extraction solvent, the extraction solvent is recycled to contact tobacco from which tobacco alkaloids are to be removed, thereby permitting continuous operation.

17. The method of claim 16, wherein the recycled extraction solvent is mixed, prior to renewed contact with tobacco, with an organic acid, monoalkali metal salts or monoammonium salts of said organic acid or a mixture thereof.

* * * * *